United States Patent [19]

Gilbert et al.

[11] Patent Number: 5,246,613
[45] Date of Patent: Sep. 21, 1993

[54] AQUEOUS ISOTROPIC PERSONAL LIQUID CLEANSING COMPOSITION WITH TRIETHANOL AMINE SOAP, SELECTED ELECTROLYTE AND SYNTHETIC SURFACANT

[75] Inventors: Lawrence A. Gilbert, West Chester; Gail Gordon, Cincinnati; James E. Taneri, West Chester, all of Ohio

[73] Assignee: The Procter & Gamble Company, Cincinnati, Ohio

[21] Appl. No.: 821,346

[22] Filed: Jan. 13, 1992

Related U.S. Application Data

[63] Continuation of Ser. No. 555,870, Jul. 20, 1990, abandoned.

[51] Int. Cl.⁵ .................. C11D 10/04; C11D 17/08
[52] U.S. Cl. ........................... 252/117; 252/108; 252/132; 252/133; 252/174.19; 252/546; 252/548; 252/550; 252/551; 252/554; 252/DIG. 5; 252/DIG. 14
[58] Field of Search .............. 252/108, DIG. 5, 117, 252/132, 133, DIG. 14, 546, 548, 550, 551, 554, 174.19

[56] References Cited

U.S. PATENT DOCUMENTS

| | | | |
|---|---|---|---|
| 3,001,944 | 9/1961 | Wei | 252/117 |
| 3,808,329 | 4/1974 | Bolich et al. | 424/70 |
| 4,310,432 | 1/1982 | Brouwer | 252/108 |
| 4,310,433 | 1/1982 | Stiros | 252/132 |
| 4,486,328 | 12/1984 | Knott et al. | 252/117 |
| 4,747,977 | 5/1988 | Whitehead et al. | 252/111 |
| 4,911,857 | 3/1990 | Machin et al. | 252/98 |
| 4,975,218 | 12/1990 | Rosser | 252/108 |

Primary Examiner—Paul Lieberman
Assistant Examiner—A. Hertzog
Attorney, Agent, or Firm—Leonard Williamson

[57] ABSTRACT

An isotropic liquid cleansing composition which is cosmetically attractive, stable and which also has excellent lather performance properties. The composition contains a water-soluble triethanolamine fatty acid soap, an electrolyte thickener selected from citrates, formates and tetraacetate, a synthetic surfactant, and water as essential components and has a neat viscosity (100%) of about 2,000 to 12,000 cps.

15 Claims, No Drawings

AQUEOUS ISOTROPIC PERSONAL LIQUID CLEANSING COMPOSITION WITH TRIETHANOL AMINE SOAP, SELECTED ELECTROLYTE AND SYNTHETIC SURFACANT

This is a continuation of application Ser. No. 07/555,870, filed on Jul. 20, 1990, now abandoned.

TECHNICAL FIELD

The present invention is related to liquid cleansing products, especially hand/bath/shower compositions which contain soap.

BACKGROUND ART

Aqueous liquid cleansing compositions per se are well known. U.S. Pat. No. 3,808,329 to Bolich et al., issued Apr. 30, 1974; discloses a mild shampoo consisting of polyethylene sorbitan mono fatty acid ester, triethanolamine (TEA) fatty acid soap, alkyl sulfate, and fatty acid ethanolamide. U.S. Pat. No. 3,001,944 to Wei, issued Sep. 26, 1961, discloses controlling viscosity of synthetic detergent-soap shampoos (e.g., Examples II & III) comprising sodium alkyl sulfate and a thinning agent such as a higher alkyl ether of polyalkylene glycol.

While it is known to use a mixture of soaps and synthetics in cleansing liquids, the selection of certain mixtures of soaps and synthetics to address a specific problem has inexhaustible potential. A stable, good lathering and milder-than-soap, liquid cleansing hand/bath/shower composition with a more soap like lather and lather drainage is still needed.

It is, therefore, an object of the present invention to provide a liquid cleansing hand/bath/shower composition which is mild, phase stable, cosmetically attractive and has a soap like lather and lather drainage.

It is a further object of the present invention to provide a liquid cleansing composition which is isotropic.

It is still a further object of the present invention to provide a liquid cleansing composition which delivers satisfactory lather.

These and other objects of the present invention will become obvious from the detailed description which follows.

SUMMARY OF THE INVENTION

The present invention relates to an isotropic liquid cleansing composition comprising from about 2% to about 12% of a water-soluble triethanolamine fatty acid soap; an electrolyte thickener selected from citrates, formates, and tetraacetate; from about 3% to about 25% of a selected water-soluble synthetic surfactants; and from about 50% to about 95% of water. The liquid cleansing composition has a neat (100%) viscosity of 2,000-12,000 cps, good lather and good lather drainage.

DETAILED DESCRIPTION OF THE INVENTION

The present invention relates to an isotropic liquid cleansing composition comprising: from about 2% to about 12%, preferably 4% to 10%, of a water-soluble triethanolamine fatty acid soap preferably having fatty acid soaps which contain a 70/30-30/70% mixture of $C_{12}$-$C_{14}$ saturated/$C_{16}$-$C_{18}$ unsaturated carbon atoms; from about 3% to about 25%, preferably 5% to 15%, of a synthetic surfactant; from about 0.3% to about 4%, preferably 0.5% to 3%, of an electrolyte salt, preferably a citrate salt; and from about 50% to about 95%, preferably about 75% to 90% of water. The liquid cleansing composition has a neat (100%) viscosity of 2,000-12,000 cps., preferably 3,000-10,000 cps, good lather and good lather drainage.

Some important attributes of the present personal cleansing product are its soap like lather and lather drainage. Another important attribute of the present invention is its perceived ease of rinsing based on lather drainage.

It has been discovered that phase stability, lathering and ease of rinsing of a liquid cleansing product is related in part to the selection of the soap and the synthetic surfactant. The desired product must then be formulated to provide the desired amount of in use lather and stability so that the product does not separate or change while stored.

The present invention relates to liquid cleansing compositions comprising from about 2% to about 12%, preferably about 3% to 10%, more preferably 4% to 8%, of a water-soluble triethanolamine (TEA) fatty acid soap. The fatty acid alkyl carbon chains for the soap are from 8 to 22 carbon atoms, preferably from 10 to 18 carbon atoms. The preferred soap is a 70/30-30/70%, preferably a 40/60-60/40%, mixture of $C_{12}$-$C_{14}$ saturated fatty acid soaps for improved lather and improved lather drainage and $C_{16}$-$C_{18}$ unsaturated fatty acid soaps primarily for mildness. TEA soaps are preferred. The liquid products containing potassium soaps are essentially free of citrate or formate salts. A preferred isotropic liquid cleansing product comprises soap and synthetic at a ratio of from about 1:1 to about 1:4, preferably from about 1.1:5 to about 1:2.

An essential component of the present compositions is from about 3% to about 25% of a synthetic surfactant. The surfactant, which may be selected from any of a wide variety of anionic (nonsoap), amphoteric, zwitterionic, nonionic and, in certain instances, cationic surfactants, and mixtures thereof, is present at a level of from about 3% to about 25%, preferably from about 5% to about 15%.

Anionic non-soap surfactants can be exemplified by the alkali metal salts of organic sulfuric reaction products having in their molecular structure an alkyl radical containing from 8 to 22 carbon atoms and a sulfonic acid or sulfuric acid ester radical (included in the term alkyl is the alkyl portion of higher acyl radicals). Preferred are the sodium, ammonium or triethanolamine alkyl sulfates, especially those obtained by sulfating the higher alcohols ($C_8$-$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water-soluble salts of condensation products of fatty acids with sarcosine; and others known in the art.

Nonionic surfactants can be broadly defined as compounds produced by the condensation of alkylene oxide groups (hydrophilic in nature) with an organic hydrophobic compound, which may be aliphatic or alkyl aromatic in nature. Examples of some classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyldecylamine oxide, dimethyltetradecylamine oxide, 3,6,9trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadaecyldimethylphosphine oxide, cetyldimethylphosphine oxide, 3-dodecoxy-2-hydroxypropyldi(2-hydroxyethyl) phosphine oxide stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetra-decylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3methoxytridecyl methyl sulfoxide, 3-hydroxytridecyl methyl sulfoxide, 3-hydroxy-4-dodecoxybutyl methyl sulfoxide.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

$$R^2-Y^{(+)}-CH_2-R^4-Z^{(-)}$$
$$\overset{(R^3)_x}{|}$$

wherein $R_2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-P-diethyl-P-3,6,9-trioxatetradexocylphosphonion]-2-hydroxypropane-1-phosphate; 3-[N,N-dipropyl-N-3-dodecoxy-2-hydroxypropylammonio]-propane1-phosphonate; 3-(N,N-dimethyl-N-hexadecylammonio)propane-1-sulfonate; 3-(N,N-dimethyl-N-hexadecylammonio)-2-hydroxypropane-1-sulfonate; 4-[N,N-di(2-hydroxyethyl)-N-(2-hydroxydodecyl)ammonio]-butane-1-carboxylate; 3-[S-ethyl-S-(3-dodecoxy-2-hydroxypropyl)sulfonio]propane-1-phosphate; 3-(P,P-dimethyl-P-dodecylphosphonio)-propane-1-phosphonate; and 5-[N,N-di(3-hydroxypropyl)-N-hexadecylammonio]2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Amphoterics such as betaines are especially preferred in the present composition.

Examples of betaines useful herein include the high alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis(2-hydroxyethyl)carboxy methyl, betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, etc. The sulfo-betaines may be represented by coco dimethyl sulfopropyl betaine, stearyl dimethyl sulfopropyl betaine, lauryl bis-(2-hydroxyethyl) sulfopropyl betaine, amido betaines amidosulfobetaines, and the like.

Many cationic surfactants are known to the art. By way of example, the following may be mentioned:
stearyldimethylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride;
laurylpyridinium chloride;
laurylisoquinolium bromide;
ditallow(hydrogenated)dimethyl ammonium chloride;
dilauryldimethyl ammonium chloride; and
stearalkonium chloride.

Many alkylpolysaccharides are known in the art. The following patents disclose examples of some of them: U.S. Pat. Nos.: 4,396,520, Payne et al., issued Aug. 2, 1983; 4,483,779, Llenardo et al., issued Nov. 20, 1984, both patents incorporated herein by reference.

Many additional nonsoap surfactants are described in McCUTCHEON'S, DETERGENTS AND EMULSIFIERS, 1990 ANNUAL, published by Allured Publishing Corporation, which is incorporated here by reference.

The above-mentioned surfactants can be used in the liquid cleansing hand/bath/shower compositions of the present invention. The anionic surfactants, particularly the alkyl sulfates, the ethoxylated alkyl sulfates and mixtures thereof are preferred. More preferred are anionic surfactants selected from the group consisting of sodium alkyl glycerol ether sulfonate, sodium lauroyl sarcosinate, sodium alkyl sulfate, sodium ethoxy (3) alkyl sulfate, and mixtures thereof.

The preferred compositions of the present invention do not contain polyoxyethylene sorbitan mono fatty acid esters as disclosed in U.S. Pat. No. 3,808,329, supra.

The preferred soap/surfactant systems of the compositions of this invention, contain from about 50% to about 150%, preferably 75% to 125%, TEA soap and surfactants based on the weight of the soap.

The preferred compositions contain an electrolyte. Electrolytes include inorganic salts (e.g., sodium chloride) as well as organic salts (e.g., sodium citrate). The amount of electrolyte varies with the type of surfactant should be present in finished product at a level of about 0.5–3%, preferably at a level of from about 1.5% to about 2.5% to provide the desired viscosity. In addition to the above-mentioned chloride and citrate salts, other salts include phosphates, sulfates, acetates, and other halogen ion salts. For TEA soap compositions, a preferred thickener is a chelating electrolyte selected from sodium or potassium citrate, sodium or potassium formate, sodium or potassium ethylene diamine tetraacetate. The citrate salt is milder to the skin than sodium chloride. The counter ions of such salts can be sodium, potassium or other monovalent cations as well as di- and trivalent cations. However, if the liquid product contains some potassium soaps, care must be taken to maintain an isotropic solution.

The amount of electrolyte thickener found useful in the present compositions is about from about 0.3% to about 4%, preferably from about 0.5% to about 3%, and more preferably from about 1.5% to about 2.5%. The thickeners are used in combination with the selected surfactants to produce the viscosity of 2,000 to 12,000 cps, preferably 3,000 to 10,000 cps.

The liquid cleansing hand/bath/shower compositions herein are in the form of liquids in which water is the principal diluent. The level of water in the compositions is typically from about 50% to about 95%, preferably greater than about 65% and more preferably greater than 75%.

The liquid cleansing hand/bath/shower compositions can contain a variety of other ingredients suitable for rendering such compositions more desirable. Such ingredients are well known to those skilled in the art, e.g., preservatives such as benzyl alcohol, methyl paraben, propyl paraben and imidazolidinyl urea; other thickeners and viscosity modifiers such as polymeric skin aids and $C_8$-$C_{18}$ ethanolamide (e.g., coconut ethanolamide) and polyvinyl alcohol; skin moisturizers such as glycerine; pH adjusting agents such as citric acid, succinic acid, phosphoric acid, sodium hydroxide, etc.; suspending agents such as magnesium/aluminum silicate; perfumes; dyes; and sequestering agents such as disodium ethylenediamine tetraacetate. One preferred form of the present compositions is a clear product. However, if desired, a pearlescer such as ethylene glycol distearate may be used to give the product a pearlescent effect.

A preferred liquid cleansing product contains from about 1% to about 5% of an alkanolamide of a fatty acid having from about 8 to about 18 carbon atoms, e.g., Lauramide DEA.

If present, the optional components individually generally comprise from about 0.001% to 10.0% by weight of the composition.

The pH of the liquid cleansing hand/bath/shower compositions herein is generally from about 7.0 to about 9.5, preferably from about 7.5 to about 8.6.

The liquid cleansing compositions of the present invention may be made using techniques known in the art. A suitable method is shown in Example I.

The liquid cleansing compositions are useful as a cleansing aid for either hands or for the entire body.

Neat Viscosity (100% Product)

Operation: (Brookfield LVF-Type Viscometer)

Pour approximately 140g of the finished product into a 150 ml beaker taking care to avoid trapping air bubbles. Check the product temperature with the thermometer - the temperature should be between 74.5°-75.5° F. (23.6°-24.2° C.). If not, a warm water or a cold water bath must be used to adjust the temperature. A common galvanized laboratory tray (depth of approximately 2½ inches) may be used. Temperatures of the baths should be 60°-65° F. for the cold and 85°-90°0 F. for the warm water. Place the beaker in the bath and stir sample gently with the thermometer, taking care to avoid generation of air bubbles. The sample is ready for analysis when a uniform temperature of 74.5°-75.5° F. exists throughout the sample. Attach spindle #4 to the viscometer. While the temperature of the sample is within the limits, carefully lower viscometer spindle #4 into the beaker. The spindle guard should not be attached. (Note: It is important that the spindle temperature is equilibrated to room temperature before inserting into the sample; allow at least 15 minutes for temperature equilibration after washing spindle.) Do not lower the spindle below the depth notch. If this occurs, raise the spindle and carefully wipe the shaft above the notch, then reinsert the spindle into the sample. Center the spindle in the beaker with the surface of the sample in the center of the spindle depth notch. Start the viscometer motor, set at 30 rpm's, wait 15 seconds, then take a meter reading. Take two additional readings. Refer to the Brookfield viscometer manual for proper operation.

Calculations:

Calculate the viscosity of the sample as follows:

$$\text{Viscosity} = A \times 200$$

A = Average of the three meter readings.
200 = Conversion factor found in the Brookfield manual for spindle #4 at 30 rpm's.

Note: When reporting the viscosity of the solution, always include the temperature 74.5°-75.5° F. (23.6°-24.2° C.).

EXAMPLES

The following examples further describe and demonstrate the preferred embodiments within the scope of the present invention. The examples are given solely for the purpose of illustration and are not to be construed as limitations of the present invention as many variations thereof are possible without departing from its spirit and scope. Unless otherwise indicated, all percentages and ratios herein are by weight and are approximations.

Performance Test Method - Liquid Hand Lather Procedure

Wash hands prior to testing to remove oils and lotions. This only has to be done at start of test or upon returning to test.

Ultimate Volume

1. Pass hand through 90°-100° F. (32°-38° C.) city water three times.
2. Dispense (using syringe) test product on this hand (use 1.7 mls of product).
3. Pass remaining hand through city water three times.
4. Spread product over palms of hand.
5. Circulate product on palm and fingers of hand three times then over back of hands once. Repeat this procedure five times.
6. Gather lather in palm of hand.
7. Add 2 mls of water to palm of hand.
8. Circulate product on palm and fingers of hand three times then over back of hands once. Repeat this procedure five times.
9. Gather lather; scrape as much lather as possible into 250 ml beaker.
10. Grade for Ultimate Volume using Liquid Grading Scale.

Ultimate Volume—Soil

Using synthetic SNS II soil (or any other test soil), dispense from syringe 0.2 mls of soil into clean, dry hands and rub into palms well.

1. Pass hand through 90°-100° F. (32°-38° C.) city water three times.
2. Dispense (using syringe) test product on this hand (use 1.7 mls of product).
3. Pass remaining hand through city water three times.
4. Spread product over palms of hand.
5. Circulate product on palm and fingers of hand three times then over back of hands once. Repeat this procedure five times.
6. Gather lather in palm of hand.
7. Add 2 mls of water to palm of hand.
8. Circulate product on palm and fingers of hand three times then over back of hands once. Repeat this procedure five times.
9. Gather lather; scrape as much lather as possible into 250 ml beaker.
10. Grade for Ultimate Volume-Soil using Liquid Grading Scale.

| Liquid Grading Scale | |
| --- | --- |
| Mls. | Grade |
| 251 mls + | 10.0 |
| 226 mls-250 mls | 9.5 |
| 201 mls-225 mls | 9.0 |
| 176 mls-200 mls | 8.5 |
| 151 mls-175 mls | 8.0 |
| 126 mls-150 mls | 7.5 |
| 101 mls-125 mls | 7.0 |
| 76 mls-100 mls | 6.5 |
| 61 mls-75 mls | 6.0 |
| 51 mls-60 mls | 5.5 |
| 36 mls-50 mls | 5.0 |
| 26 mls-35 mls | 4.5 |
| 25 mls | 4.0 |
| 20 mls | 3.5 |
| 15 mls | 3.0 |
| 10 mls | 2.0 |
| 5 mls | 1.0 |

In addition to the examples is a Lather Draining Test Procedure that demonstrate the differences in lather drainage for the TEA soap products of this invention vs. an all synthetic based liquid. An all liquid soap base product is the standard. The product of this invention is also milder than the all soap base standard, and is a better lathering product than the all synthetic product.

EXAMPLE I

A preferred isotropic liquid personal cleansing product formula was made as follows:

Synthetic/Soap Batch Making Process

1. Add deionized water.
2. Heat to 160° F. (~71° C.).
3. Melt Fatty Acid mix at 120° F. (~49° C.).
4. Add TEA (liquid, 100% active).
5. Add Fatty Acid to water/TEA mix.
6. Mix for 15 minutes.
7. Cool to 130° F. (~56° C.).
8. Add NaALS (powder, 100% active) as cooling.
9. Add the following as cooling:
   Betaine (liquid, 35% active)
   LDEA (liquid, 100% active)
   EDTA (powder, 100% active)
   Glydant (liquid, 100% active
   Lytron (liquid, 40% active)
10. Mix for 20 minutes.
11. Once temperature is less than 110° F. (~43° C.) add perfume (liquid, 100% active).
12. Mix 10 minutes.
13. Cool to 80° F. (~27° C.).
14. Add 95% of sodium citrate and sodium chloride (powder, 100% active)
15. Mix for 30 minutes.
16. Check viscosity.
17. Adjust viscosity if necessary with NaCl to about 5,000 cps.

The pH (10% solution) of Example I is 8.0.

| Liquid Synthetic/Soap Formulas - Examples I & II | | |
|---|---|---|
| Ingredient | Example I Wt. % | Example II Wt. % |
| Sodium Lauryl Sulfate (NaALS) | 8.00 | 8.00 |
| Triethanol Amine:Lauric/Oleic Soap | 5.00 | — |
| Potassium:Lauric/Oleic Soap | — | 5.00 |
| Lauramide DEA (LDEA) | 1.50 | 1.50 |
| Cocamidopropyl Betaine | 1.50 | 1.50 |
| NaCl | 1.60 | 1.50 |
| Potassium Citrate | 1.00 | 1.00 |
| Na EDTA | 0.10 | 0.10 |
| DMDM Hydantoin (Glydant) | 0.20 | 0.20 |
| Perfume | 0.30 | 0.30 |
| Water | 80.80 | Balance |
| Viscosity (cps.): | 3,500 | N/A |
| pH (10% solution): | 8.0 | 9.6 |

EXPERIMENTAL EXAMPLE II

A product is made with potassium lauric/oleic soap instead of TEA soap using the same making process as used in Example I. This liquid product, made with potassium soap, Experimental Example II, crystallizes. The TEA soap (Example I) remains a clear isotropic solution.

A product similar to Experimental Example II, Experimental Example VII, but without the potassium citrate remains an isotropic solution. The TEA based liquid product, Example I, is expected to be milder, as well as more stable, than a potassium soap based product like Example II.

COMPARATIVE EXAMPLE III

A third product formula is made using a similar procedure as set out in Example I, but with an all synthetic surfactant system. The formula is the following:

| All Synthetic Formula - Example III | |
|---|---|
| Ingredient | Wt. % |
| Ammonium Laureth Sulfate | 8.00 |
| Ammonium Lauryl Sulfate | 4.00 |
| Lauramide DEA | 1.50 |
| Cocamidopropyl Betaine | 1.50 |
| NaCl (Thickener) | 1.05 |
| Lytron (Opacifier) | 0.40 |
| Na EDTA | 0.10 |
| Glydant (Preservative) | 0.20 |
| Perfume | 0.20 |
| Citric Acid | 0.08 |
| Water | Balance |
| Lather: Ultimate Volume w/Soil | 5.5 |
| Ultimate Volume | 8.0 |
| Viscosity: | 6,200 |
| Description: | Opaque Isotropic |

The Comparative Example III, all synthetic, making process is as follows:
1. Add deionied water at 55°-100° F. (~10°38° C.)
2. Add:
   AE$_3$S (liquid, 28% active)
   ALS (liquid, 25% active)
   Betaine (liquid, 35% active)
   LDEA (liquid, 100% active
Note: Steps 1 and 2 can be done in either order.
3. Mix for 10 minutes.
4. Add:
   EDTA (powder, 100% active)
   Glydant (liquid, 100% active
   Lytron (liquid, 40% active)
   Citric Acid (powder, 100% active)
5. Mix 10 minutes.
6. Check pH.
7. Readjust pH to 6.8 if necessary with Citric Acid.
8. Add perfume (liquid, 100% active).
9. Mix 10 minutes.
10. Add 95% of NaCl (powder, 100% active).
11. Mix for 30 minutes.
12. Check viscosity.
13. Adjust viscosity if necessary with NaCl to about 5,000 cps.

COMPARATIVE EXAMPLE IV

In this Example the fatty acids are neutralized with caustic potash (potassium hydroxide) to provide an all soap liquid cleanser. This is the standard product for a good lathering and good lather drainage.

| Comparative Example IV | | |
|---|---|---|
| Ingredient | Function | Formula Wt. % |
| Lauric/Oleic Soap | Surfactant | 25.50 |
| Lauric/Oleic Fatty Acid | Surfactant | 1.80 |
| Glycerine | Conditioner | 2.00 |
| Na EDTA | Preservative | 0.10 |
| K Acetate | Thickener | 3.85 |
| Lytron | Opacifier | 0.40 |
| Kathon | Preservative | 0.03 |
| Perfume | Odor | 0.10 |
| Water | | 66.22 |

The pH is about 9.4.

EXPERIMENTAL EXAMPLE V

This one is similar to Example VII below except that: (1) potassium:myristic soap is used instead of the mixture of lauric and oleic potassium soaps; (2) the NaCl level is 0.2%; and (3) no potassium citrate is used. The liquid product, Example V, turns into a paste after cooling while the product of Example VII remains a clear isotropic solution.

| Liquid Synthetic/Soap Formula - Comparative Example V | |
|---|---|
| Ingredient | Wt. % |
| Sodium Lauryl Sulfate (NaALS) | 8.00 |
| Potassium:Myristic ($C_{14}$) Soap | 5.00 |
| Lauramide DEA (LDEA) | 1.50 |
| Cocamidopropyl Betaine | 1.50 |
| NaCl | 0.20 |
| Na EDTA | 0.10 |
| DMDM Hydantoin (Glydant) | 0.20 |
| Perfume | 0.10 |
| Water | Balance |
| Description: | White Paste |

The pH is about 8.9.

EXAMPLE VI

Example VI is an experimental liquid product. The ultimate volume of lather with and without soil is about 6.0 and 7.5, respectively. The ultimate soil volume lather for Example VI is better than that of all synthetic Comparative Example III, 6.0 vs. 5.5, respectively. The ultimate soil volume lather is more important than the lather volume without soil because it is soiled hands that need the lather. It is expected that the soil volume lather would be the same when about 1% citrate is used in place of 1% NaCl.

| Synthetic/Soap Formula - Example VI | |
|---|---|
| Ingredient | Wt. % |
| Sodium Lauryl Sulfate | 8.00 |
| TEA:Lauric/Oleic Soap | 5.00 |
| Lauramide DEA | 1.50 |
| Cocamidopropyl Betaine | 1.50 |
| NaCl (Thickener) | 1.98 |
| Lytron (Opacifier) | 0.40 |
| Na EDTA | 0.10 |
| Glydant (Preservative) | 0.20 |
| Perfume | 0.30 |
| Water | Balance |
| Lather: Ultimate Volume w/Soil | 6.0 |
| Ultimate Volume | 7.5 |
| Viscosity: | 4,400 |

The pH is 7.9.

Lather Drainage Test

Procedure:

Use City water (9-12 grains) at 95°-100° F. (~38° C.) and an oval bottom sink. (A flat bottom sink should be avoided.)

Leave water running at moderate pressure.
1. Wet hands under running water.
2. Put one pump (1.8 g) of liquid soap on hands. Add 2 cc water with a 10 cc syringe. Rotate hands over one another for 15 seconds away from the water.
3. Do not rinse hands, repeat above steps three more times for a total of four times. Be careful not to lose lather down the sink.
4. After completing the fourth cycle rinse hands completely under running water.
5. With a timer, keep track of how much time (secs.) it takes all the suds in the sink to go down the drain. Record time.

The liquid cleansers of Examples III, IV and VI are tested. Example VI of this invention with a mixed TEA soap and synthetic surfactant system is better in lather and lather drainage than the all synthetic based Comparative Example III.

| Seconds for Lather to Drain Down Sink | |
|---|---|
| Example III | 45 |
| Example IV | 12 |
| Example VI | 24 |

The above timings are the average of ten runs. This shows that the product of the present invention, Example VI, has improved lather dissipation and drainage, over the all synthetic Comparative Example III which contains a comparable level of total surfactant. Comparative Example IV is the all soap based standard liquid product.

Although Comparative Example IV is best in terms of lather drainage, it is not as mild as Example VI. Example VI is slightly down to Comparative Example IV in soil lather (6 vs. 7), yet requires significantly less overall total soap and surfactant (16% vs. 27.3%).

EXAMPLES VII & VIII

These Examples are similar to Example I and VI, except that potassium soap is used instead of the mixture of TEA soaps, and no NaCl is added.

| Ingredient | I Wt. % | VII Wt. % | VIII Wt. % |
|---|---|---|---|
| Sodium Lauryl Sulfate | 8.0 | 8.0 | 8.0 |
| TEA:Lauric/Oleic Soap | 5.0 | — | — |
| Potassium:Lauric/Oleic Soap | — | 5.0 | 5.0 |
| Lauramide DEA | 1.5 | 1.5 | 1.5 |
| Cocamidopropyl Betaine | 1.5 | 1.5 | 1.5 |
| NaCl (Thickener) | 1.6 | — | — |
| Potassium Citrate | 1.0 | — | 1.0 |
| Na EDTA | 0.1 | 0.1 | 0.1 |
| Glydant (Preservative) | 0.2 | 0.2 | 0.2 |
| Perfume | 0.3 | 0.1 | 0.1 |
| Water | 80.80 | Balance | Balance |
| Viscosity: | 3,500 | <100 | N/A |
| Description: | Isotropic | Isotropic | Crystalline |
| pH (10% solution) | 8.0 | 9.8 | 9.7 |

No potassium citrate or sodium chloride are used in Example VII. When 1.0% of potassium citrate is used in Example VIII, the isotropic liquid (Example VII) turns crystalline. The viscosity of Example VII is increased to 3,500 cps with the addition of NaCl and remains an isotropic solution.

What is claimed is:

1. An isotropic liquid hand/bath/shower cleansing product consisting essentially of:
   A. from about 2% to about 12% of a water-soluble triethanolamine fatty acid soap;
   B. from about 3% to about 25% of a synthetic surfactant; said synthetic surfactant comprising at least about 3% anionic surfactant by weight of said product;

C. from about 0.3% to about 4.0% of an electrolyte selected from the group consisting of: citrates, formates, and tetraacetates;

D. from about 50% to about 95% water; and wherein said product has a neat product viscosity (100%) of from about 2,000 cps to about 12,000 cps; and wherein the anionic surfactant is selected from the group consisting of sodium alkyl glycerol ether sulfonate, sodium lauryl sarcosinate, sodium alkyl sulfate, sodium ethoxy (1-12) alkyl sulfate and mixtures thereof; and wherein said synthetic surfactant includes about 0.5-4% fatty acid ethanolamide and about 0.5-4% of a betaine selected from the group consisting of: coco dimethyl carboxymethyl betaine, lauryl dimethyl carboxymethyl betaine, lauryl dimethyl alpha-carboxyethyl betaine, cetyl dimethyl carboxymethyl betaine, lauryl bis(2-hydroxyethyl)carboxy methyl betaine, stearyl bis-(2-hydroxypropyl) carboxymethyl betaine, oleyl dimethyl gamma-carboxypropyl betaine, and lauryl bis-(2-hydroxypropyl) alpha-carboxyethyl betaine.

2. An isotropic liquid cleansing product according to claim 1 wherein said citrate salt is present at a level of about 0.5% to about 2.0%.

3. An isotropic liquid cleansing product according to claim 2 wherein said soap said synthetic has a ratio of from about 1:1 to about 1:4.

4. A liquid cleansing product according to claim 3 wherein the synthetic surfactant is present at a level from about 5% to about 15%.

5. An isotropic liquid cleansing product according to claim 1 wherein said product has a neat viscosity (100%) of from about 3,000 cps to about 10,000 cps.

6. An isotropic liquid cleansing product according to claim 5 wherein said product contains from about 1% to about 5% of an alkanolamide of a fatty acid having from about 8 to about 18 carbon atoms.

7. An isotropic liquid cleansing product according to claim 1 wherein said composition contains from about 0.5% to about 3.0% of a citrate salt and said water is from about 75% to about 95%.

8. An isotropic liquid cleansing product according to claim 7 wherein said product contains from about 0.1% to about 10% of an opacifier.

9. An isotropic liquid cleansing product according to claim 1 wherein the surfactant comprising at least about 5% anionic surfactant.

10. An isotropic liquid cleansing product comprising:

A. from about 2% to about 12% of a water-soluble soap selected from the group consisting of triethanolamine and potassium fatty acid soap and mixtures thereof; wherein said fatty acid contains a 70/30-30/70% mixture of $C_{12}$-$C_{14}$ saturated/$C_{16}$-$C_{18}$ unsaturated carbon atoms;

B. from about 3% to about 25% of a synthetic surfactant;

C. from about 75% to about 95% water; and wherein when said soap is essentially potassium fatty acid soap, said product is essentially free of citrates and formates; and wherein said product has a neat product viscosity (100%) of from about 2,000 cps to about 12,000 cps.; and wherein said synthetic surfactant includes an anionic surfactant selected from the group consisting of sodium alkyl glycerol ether sulfonate, sodium lauryl sarcosinate, sodium alkyl sulfate, sodium ethoxy (1-12) alkyl sulfate and mixtures thereof; and wherein said synthetic surfactant includes about 0.5-4% fatty acid ethanolamide and about 0.5-4% of a betaine selected from the group consisting of: coco dimethyl carboxymethyl betaine, lauryl dimethyl carboxymethyl betaine, lauryl dimethyl alpha-carboxyethyl betaine, cetyl dimethyl carboxymethyl betaine, lauryl bis(2-hydroxyethyl)carboxy methyl betaine, stearyl bis-(2-hydroxypropyl) carboxymethyl betaine, oleyl dimethyl gamma-carboxypropyl betaine, and lauryl bis-(2-hydroxypropyl) alpha-carboxyethyl betaine.

11. An isotropic liquid hand/bath/shower cleansing product of claim 10 wherein said viscosity is form about 3,500 cps to about 10,000 cps.

12. An isotropic liquid hand/bath/shower cleansing product consisting essentially of:

A. from about 2% to about 12% of a water-soluble soap selected from the group consisting of: triethanolamine and potassium fatty acid soap and mixtures thereof;

B. from about 3% to about 15% of a synthetic surfactant;

C. from about 0.3% to about 4.0% of an inorganic electrolyte;

D. from about 75% to about 95% water; and wherein when said soap is essentially potassium fatty acid soap, and wherein said product is essentially free of citrates and formates; and wherein said product has a neat product viscosity (100%) of from about 2,000 cps to about 12,000 cps.; and wherein said synthetic surfactant includes an anionic surfactant selected from the group consisting of sodium alkyl glycerol ether sulfonate, sodium lauryl sarcosinate, sodium alkyl sulfate, sodium ethoxy (1-12) alkyl sulfate and mixtures thereof; and wherein said synthetic surfactant includes about 0.5-4% fatty acid ethanolamide and about 0.5-4% of a betaine selected from the group consisting of: coco dimethyl carboxymethyl betaine, lauryl dimethyl carboxymethyl betaine, lauryl dimethyl alpha-carboxyethyl betaine, cetyl dimethyl carboxymethyl betaine, lauryl bis(2-hydroxyethyl)carboxy methyl betaine, stearyl bis-(2-hydroxypropyl) carboxymethyl betaine, oleyl dimethyl gamma-carboxypropyl betaine, and lauryl bis-(2-hydroxypropyl) alpha-carboxyethyl betaine.

13. An isotropic liquid hand/bath/shower cleansing product of claim 12 wherein said viscosity is from about 3,500 cps to about 10,000 cps.

14. An isotropic liquid hand/bath/shower cleansing product consisting essentially of:

A. from about 2% to about 12% of a water-soluble triethanolamine fatty acid soap;

B. from about 3% to about 15% of a synthetic surfactant;

C. from about 0.3% to about 4.0% of an electrolyte selected from the group consisting of: citrates, formates, and tetraacetates and mixtures thereof;

D. from about 75% to about 95% water; and wherein said product has a neat product viscosity (100%) of from about 2,000 cps to about 12,000 cps.; and wherein said synthetic surfactant includes an anionic surfactant selected from the group consisting of sodium alkyl glycerol ether sulfonate, sodium lauryl sarcosinate, sodium alkyl sulfate, sodium ethoxy (1-12) alkyl sulfate and mixtures thereof; and wherein said synthetic surfactant includes about 0.5-4% fatty acid ethanolamide and about 0.5-4% of a betaine selected from the group consisting of: coco dimethyl carboxymethyl betaine, lauryl dimethyl carboxymethyl betaine, lauryl dimethyl alpha-carboxyethyl betaine, cetyl dimethyl carboxymethyl betaine, lauryl bis(2- hydroxyethyl)carboxy methyl betaine, stearyl bis-(2-hydroxypropyl) carboxymethyl betaine, oleyl dimethyl gamma-carboxypropyl betaine, and lauryl bis-(2-hydroxypropyl) alpha-carboxyethyl betaine.

15. An isotropic liquid hand/bath/shower cleansing product consisting essentially of:
- A. from about 2% to about 12% of a water-soluble triethanolamine fatty acid soap;
- B. from about 3% to about 15% of a synthetic surfactant;
- C. from about 0.3% to about 4.0% of an electrolyte selected from the group consisting of: citrates, formates and mixtures thereof;
- D. from about 75% to about 95% water; and wherein said product has a neat product viscosity (100%) of from about 3,000 cps to about 12,000 cps.; and wherein said synthetic surfactant includes an anionic surfactant selected from the group consisting of sodium alkyl glycerol ether sulfonate, sodium lauryl sarcosinate, sodium alkyl sulfate, sodium ethoxy (1–12) alkyl sulfate and mixtures thereof; and wherein said synthetic surfactant includes about 0.5–4% fatty acid ethanolamide and about 0.5–4% of a betaine selected from the group consisting of: coco dimethyl carboxymethyl betaine, lauryl dimethyl carboxymethyl betaine, lauryl dimethyl alpha-carboxyethyl betaine, cetyl dimethyl carboxymethyl betaine, lauryl bis(2-hydroxyethyl)carboxy methyl betaine, stearyl bis-(2-hydroxypropyl) carboxymethyl betaine, oleyl dimethyl gamma-carboxypropyl betaine, and lauryl bis-(2-hydroxypropyl) alpha-carboxyethyl betaine.

* * * * *

UNITED STATES PATENT AND TRADEMARK OFFICE
CERTIFICATE OF CORRECTION

PATENT NO. : 5,246,613

DATED : September 21, 1993

INVENTOR(S) : Lawrence A. Gilbert; Gail Gordon; and James E. Taneri

It is certified that error appears in the above-identified patent and that said Letters Patent is hereby corrected as shown below:

TITLE PAGE:

[54] Title: "SURFACANT" should read -- SURFACTANT --.

Col. 4, line 6, "3,6,9-trioxaoctadaecyldimethylphosphine" should read -- 3,6,9-trioxaoctadecyldimethylphosphine --.

Col. 4, line 63, "ocylphosphonion]" should read -- ocylphosphonio]--.

Col. 7, line 21, "90°0 F." should read -- 90°F. --.

IN THE CLAIMS:

Col. 13, line 9, "lauryl" should read -- lauroyl --.

Col. 13, line 46, "comprising" should read -- comprises --.

Col. 13, line 65, "lauryl" should read -- lauroyl --.

Col. 14, line 10, "form" should read -- from --.

Col. 14, line 30, "lauryl" should read -- lauroyl --.

Signed and Sealed this

Ninth Day of July, 1996

*Attest:*

BRUCE LEHMAN

*Attesting Officer*     *Commissioner of Patents and Trademarks*